US00PP31570P2

(12) United States Plant Patent
Hartman

(10) Patent No.: US PP31,570 P2
(45) Date of Patent: Mar. 17, 2020

(54) ***CALADIUM* PLANT NAMED 'XPLOSION'**

(50) Latin Name: ***Caladium* X *hortulanum***
Varietal Denomination: Xplosion

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/501,045

(22) Filed: Feb. 13, 2019

(51) Int. Cl.
*A01H 5/02* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Caladium* plant named 'Xplosion', characterized by its intermediate height; mounding habit; dense and bushy appearance; vigorous growth habit and rapid growth rate; lance-type leaves that are dark green tinged with greyed purple in color with red purple to dark red-colored venation and interveinal areas that are white in color with light red-colored spots; with development leaves become lighter green and less tinged with greyed purple; and leaf petioles that are greyed red, green and greyed green in color with dark brown-colored streaks and stipples.

4 Drawing Sheets

Botanical designation: *Caladium* X *hortulanum*.
Cultivar denomination: 'XPLOSION'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'Xplosion'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Fla. of *Caladium* X *hortulanum* 'Candy Cane', not patented, as the female, or seed, parent with *Caladium* X *hortulanum* 'Scarlet Flame', disclosed in U.S. Plant Pat. No. 25,419, as the male, or pollen, parent. The new *Caladium* plant was discovered and selected by the Inventor as a single plant within the progeny of the stated cross-pollination in a controlled outdoor nursery environment in Zolfo Springs, Fla. in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Xplosion'. These characteristics in combination distinguish 'Xplosion' as a new and distinct *Caladium* plant:

1. Intermediate in height and mounding habit; dense and bushy appearance.
2. Vigorous growth habit and rapid growth rate.
3. Lance-type leaves that are dark green tinged with greyed purple in color with red purple to dark red-colored venation and interveinal areas that are white in color with light red-colored spots; with development leaves become lighter green and less tinged with greyed purple.
4. Petioles that are greyed red, green and greyed green in color with dark brown-colored streaks and stipples.

Plants of the new *Caladium* differ primarily from plants of the female parent, 'Candy Cane', in the following characteristics:

1. Plants of the new *Caladium* grow faster than plants of 'Candy Cane'.
2. Plants of the new *Caladium* produce larger and more tubers per plant than plants of 'Candy Cane'.
3. Plants of the new *Caladium* and 'Candy Cane' differ in leaf color as leaves of plants of the new *Caladium* are dark green tinged with greyed purple in color with red purple to dark red-colored venation and interveinal areas that are white in color with light red-colored spots whereas leaves of plants of 'Candy Cane' are greenish white in color variably flushed with light red with dark red to dark greyed purple-colored venation and narrow green-colored margins.

Plants of the new *Caladium* differ primarily from plants of the male parent, 'Scarlet Flame', in the following characteristics:

1. Leaves of plants of the new *Caladium* do not split forming "double leaves" whereas leaves of plants of 'Scarlet Flame' are prone to splitting forming "double leaves".
2. Plants of the new *Caladium* and 'Scarlet Flame' differ in leaf color as leaves of plants of the new *Caladium* are dark green tinged with greyed purple in color with red purple to dark red-colored venation and interveinal areas that are white in color with light red-colored spots whereas leaves of plants of 'Scarlet Flame' are dark green in color with rose red-colored venation and pink and rose red-colored spots and blotches.

Plants of the new *Caladium* can be compared to plants of *Caladium* X *hortulanum* 'Florida Sweetheart', disclosed in U.S. Plant Pat. No. 8,526. In side-by-side comparisons, plants of the new *Caladium* differ primarily from plants of 'Florida Sweetheart' in the following characteristics:

1. Plants of the new *Caladium* grow faster than plants of 'Florida Sweetheart'.
2. Plants of the new *Caladium* and 'Florida Sweetheart' differ in leaf color as leaves of plants of the new *Caladium* are dark green tinged with greyed purple in color with red purple to dark red-colored venation and interveinal areas that are white in color with light red-colored spots whereas leaves of plants of 'Florida Sweetheart' have dark pink-colored venation, rose pink-colored interveinal areas with greenish white-colored margins.

Plants of the new *Caladium* can also be compared to plants of *Caladium* X *hortulanum* 'Puppy Love', disclosed in U.S. Plant Pat. No. 25,424. In side-by-side comparisons, plants of the new *Caladium* differ primarily from plants of 'Puppy Love' in leaf color as leaves of plants of the new *Caladium* are dark green tinged with greyed purple in color with red purple to dark red-colored venation surrounded with light red and interveinal areas that are white in color with light red-colored spots whereas leaves of plants of 'Puppy Love' are rose red in color with rose red-colored venation and green to whitish green-colored margins.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Xplosion' in a container and grown in a shadehouse (tuber de-eyed).

The photograph at the top of the second sheet is a comparison view of typical plants of 'Xplosion' grown in containers; the plant on the left has not had its tuber de-eyed and the plant on the right has had its tuber de-eyed prior to planting.

The photograph at the bottom of the second sheet is a side perspective view of typical plants of 'Xplosion' grown in an open production field.

The photograph at the top of the third sheet is a comparison view of typical potted plants of the female parent, 'Candy Cane' (left), 'Xplosion' (center) and the male parent, 'Scarlet Flame' (right).

The photograph at the bottom of the third sheet is a comparison view of typical potted plants of 'Florida Sweetheart' (right), 'Xplosion' (center) and 'Puppy Love' (left).

The photograph at the top of the fourth sheet is a close-up view of typical freshly-harvested tubers with roots and leaf petioles of 'Xplosion'.

The photograph at the bottom of the fourth sheet is a close-up view of a typical inflorescence of 'Xplosion'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shadehouse were eight weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Xplosion'.

Parentage:

*Female, or seed, parent.*—*Caladium* X *hortulanum* 'Candy Cane', not patented.

*Male, or pollen, parent.*—*Caladium* X *hortulanum* 'Scarlet Flame', disclosed in U.S. Plant Pat. No. 25,419.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments elliptic to round in shape. Height: About 2.6 cm to 3.3 cm. Diameter: About 5.6 cm to 9.9 cm. Segment height: About 2.3 cm. Segment diameter: About 1.6 cm to 2.2 cm. Axillary bud size: About 3.5 mm by 4 mm. Texture: Thick, starchy; somewhat brittle. Color: Epidermis, freshly-harvested: Close to 159B and 159C tinged with 36B. Epidermis, dried: Close to 200A. Cortical tissue: Close to 10C and 10D. Axillary buds: Close to 39B to 39C. Root description: Thick, fleshy contractile roots with few lateral branches; color, close to N155D. Rooting habit: Dense.

Plant description:

*Plant type*.—Herbaceous perennial; suitable as a potted plant in containers 15-cm to 25-cm and suitable as a landscape plant in shaded areas.

*Plant and growth habit*.—Intermediate in height and mounded plant habit; inverted triangle and wider than tall; dense and bushy appearance; vigorous growth habit and rapid growth rate; potted plants finish in saleable form in about six to seven weeks after planting tubers; leaf petioles and leaves arise from one or more growing points on tubers; leaf petioles initially upright and arching outwardly with development.

*Plant height, from soil level to top of foliar plane, shadehouse-grown potted plants*.—About 23 cm to 27 cm.

*Plant height, from soil level to top of inflorescences, shadehouse-grown potted plants*.—About 32 cm.

*Plant diameter or spread, shadehouse-grown potted plants*.—About 36 cm to 41 cm.

*Number of shoots per plant, shadehouse-grown potted plants, tubers not de-eyed*.—About six to seven develop per #1 tuber.

*Number of shoots per plant, shadehouse-grown potted plants, tubers de-eyed*.—About nine to ten develop per #1 tuber.

*Cataphylls, shadehouse-grown potted plants*.—Length: About 3.5 cm to 5 cm. Width: About 1.3 cm to 1.8 cm. Shape: Lanceolate to elliptic, elongate. Apex: Acute. Base: Sheathing the stem. Color, inner surface: Close to 155C and 196D; colors and patterns on the outer surface are visible on the inner surface. Color, outer surface: Close to 148A and 148B tinged with N170D variably streaked and stippled with 200A; with development, color becoming closer to N199C and 199A.

Leaf description:

*Arrangement and type*.—Alternate; simple; lance-type.

*Length, shadehouse-grown potted plants*.—About 16.2 cm to 18.5 cm.

*Width, shadehouse-grown potted plants*.—About 10 cm to 12.9 cm; when flattened, about 11 cm to 13.7 cm.

*Shape*.—Ovate.

*Apex*.—Acuminate to acute.

*Base*.—Sagittate to peltate.

*Margin*.—Entire; mostly flat with broad undulations.

*Texture and luster, upper surface*.—Smooth, glabrous; dull sheen.

*Texture and luster, lower surface*.—Smooth, glabous; glaucous; dull sheen.

*Venation pattern*.—Pinnate.

*Color, shadehouse-grown potted plants*.—Developing and fully developed leaves, upper surface: Background: Darker than 147A tinged with 187A. Leaf edge: Close to 187A. Basal notch: Close to 187A to 187B. Midvein and lateral venation: Close to 59B, 59C and 53A; areas surrounding venation, close to 51B; secondary venation, close to 187A. Interveinal areas: Close to 155C and 147A. Random spots: Close to 54D, 155C and 147A. With development, background color is closer to darker than 147A without the greyed purple tinge and interveinal areas are closer to 148C, 147B and 147C. Developing and fully developed leaves, lower surface: Background: Close to 191A tinged with N189A. Leaf edge: Close to 183A. Basal notch: Close to 187B. Midvein: Close to 36D and N155C. Primary venation: Close to 36D, N155C and 145D. Interveinal areas: Random areas that are close to 155C and N155C tinged with 36D. Random spots: Close to 191A.

*Petioles*.—Aspect: Initially upright and straight and outwardly arching with development; flexible. Length, shadehouse-grown potted plants: About 13 cm to 21.5 cm. Diameter, distally, shadehouse-grown potted plants: About 3.5 mm to 5 mm. Diameter, proximally, shadehouse-grown potted plants: About 5.5 mm to 8.5 mm. Texture and luster: Smooth, glabrous; slightly glaucous, distally, glaucous; dull. Color, shadehouse-grown potted plants, when developing and fully developed: Proximally, close to 181C to 181D, 182C, 182D, 147B to 147C, 195A and 199D streaked and stippled with 200A; distally (just below leaf junction), close to 147C to 147D variably tinged with close to 182D. Wing length, shadehouse-grown potted plants: About 3.2 cm to 4.2 cm. Wing diameter, shadehouse-grown potted plants: About 6.8 mm to 7.5 mm. Texture and luster, inner and outer surfaces: Smooth, glabrous; dull. Wing color, shadehouse-grown potted plants: Inner surface: Close to 155C and 196D; colors and patterns on the outer surface are visible on the inner surface. Outer surface: Close to 148A, 147A and N170D tinged with 181C stippled and streaked with 200A.

Inflorescence description: Inflorescences observed on four week-old shadehouse-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with mint and camphor notes.

*Natural flowering season and flower longevity*.—Plants of the new *Caladium* typically flower during the spring and summer in central Florida; flowers develop about four weeks after growth commences; inflorescences last about three days before fading; inflorescences persistent.

*Spathe*.—Length, overall: About 12 cm. Length, distal open portion: About 7.5 cm. Length, proximal closed portion: About 4.5 cm. Width, distal open portion: About 3.6 cm. Depth, distal open portion: About 2.3 cm. Width, at constriction: About 1.6 cm. Width, proximal closed portion: About 2.9 cm. Shape, open portion: Elliptic. Apex: Acuminate. Base: Acute. Margin: Entire; smooth. Texture and luster, front surface: Smooth, glabrous; dull. Texture and luster, rear surface: Smooth, glabrous; dull; proximally, glaucous. Color, front surface: Distal open portion: Close to 157C and 155C; with development, color becoming closer to 200C. Proximal closed portion: Close to 147B; color does not change with development. Color, rear surface: Distal open portion: Close to 145C tinged with 147D and marbled and streaked with 155C; color does not change with development. Proximal closed portion: Close to 147B, 147C and 147D; towards the margins, tinged with 183D; color does not change with development.

*Spadix*.—Length, overall: About 9.3 cm. Length, male flower zone: About 5.7 cm. Length, sterile zone: About 2 cm. Length, female flower zone: About 1.6 cm. Diameter, male flower zone: About 1 cm. Diameter, sterile flower zone: About 7 mm. Diameter, female flower zone: About 1 cm. Shape: Spindle-shaped. Apex: Rounded. Base: Obtuse. Aspect: Upright. Color, mature, male zone: Close to 158D. Color, mature, sterile zone: Close to 158D. Color, mature, female zone: Close to 159C. Male flowers: Quantity per spadix: About 160. Shape: Obovate. Height: About 3.1 mm. Diameter: About 2.2 mm to 3 mm. Pollen amount: Abundant. Pollen color: Close to 11B. Female flowers: Quantity per spadix: About 140. Shape: Obovate to ovate. Height: About 2 mm to 2.2 mm. Diameter: About 2 mm. Stigma color: Close to 159C. Ovary color: Close to 159A.

*Scape*.—Length: About 20 cm. Diameter: About 6 mm. Strength: Sturdy; flexible. Aspect: Mostly erect. Texture and luster: Smooth, glabrous; dull; distally, glaucous. Color: Close to 181D lightly stippled and streaked with 200A; distally, close to 147D tinged with 191D faintly and variably stippled and streaked with 182A.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'Xplosion' as illustrated and described.

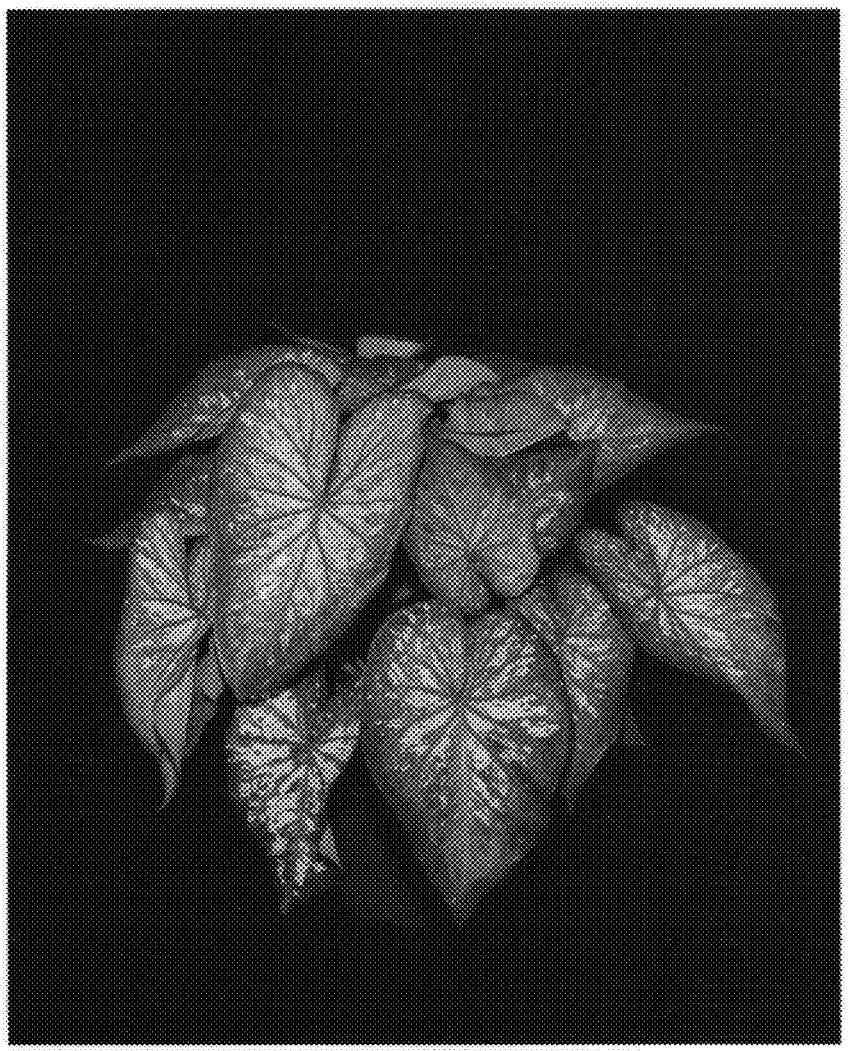

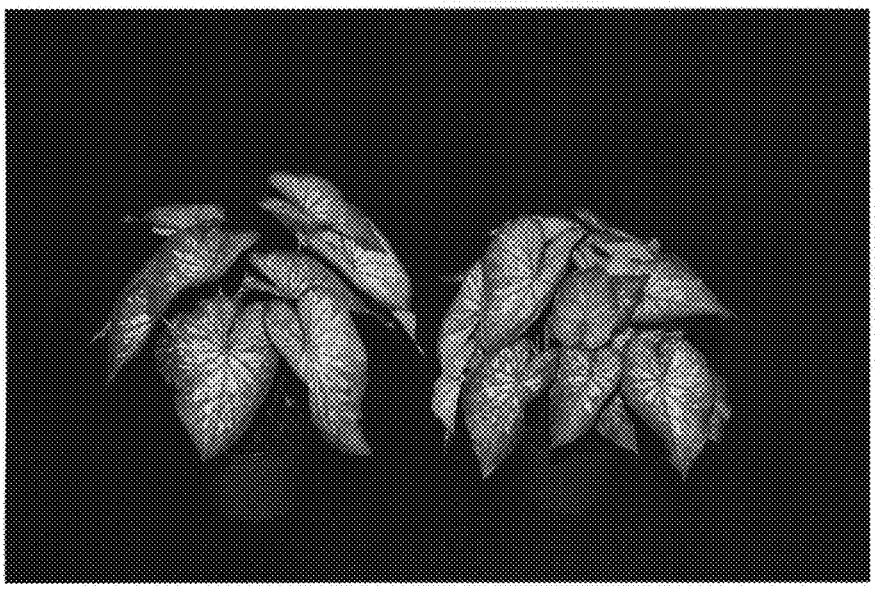
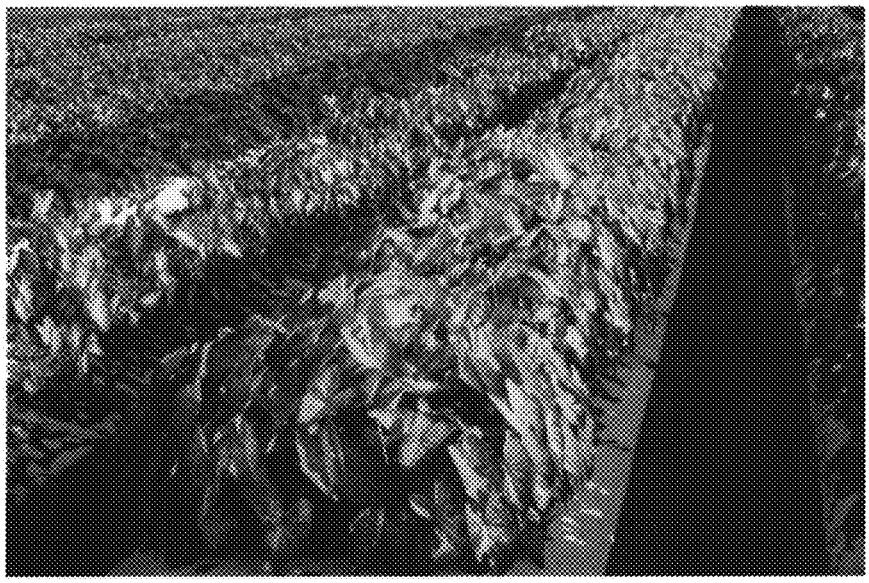

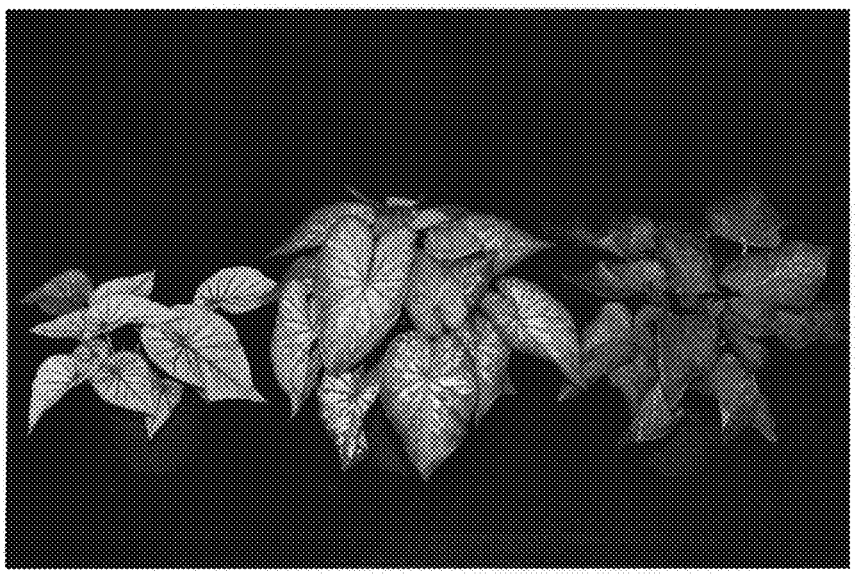
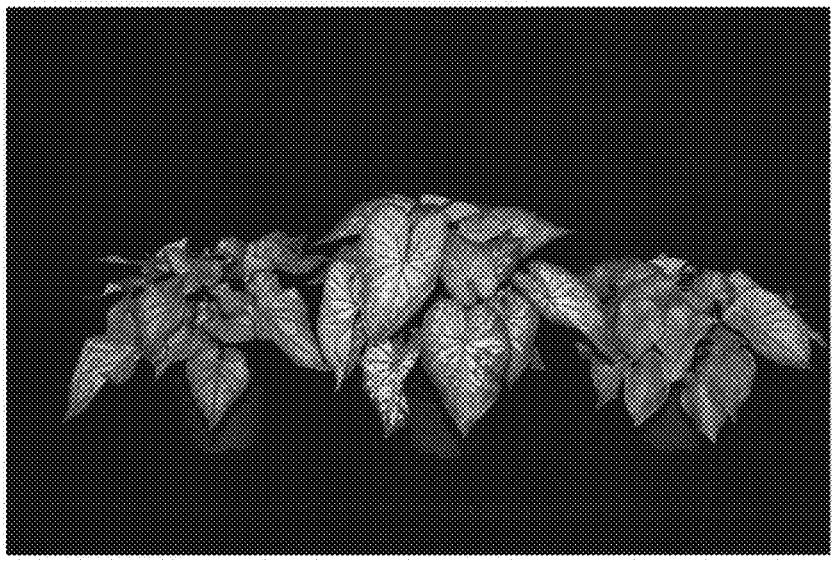

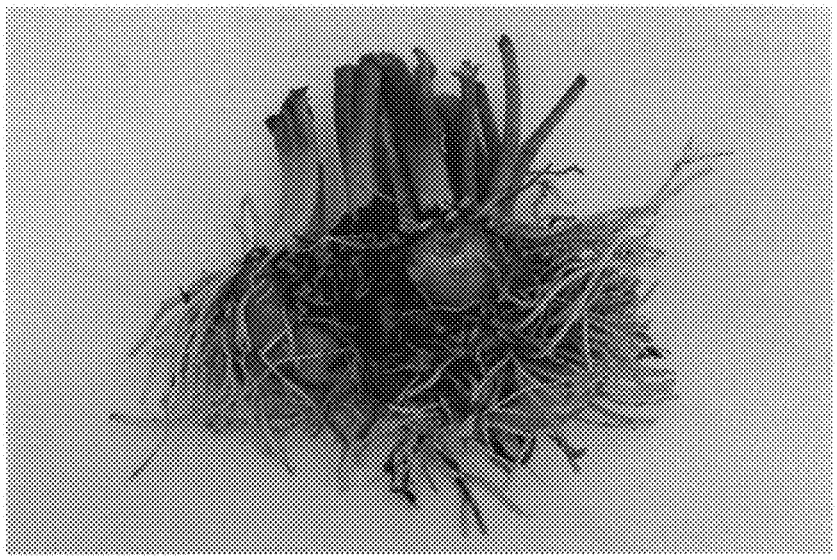
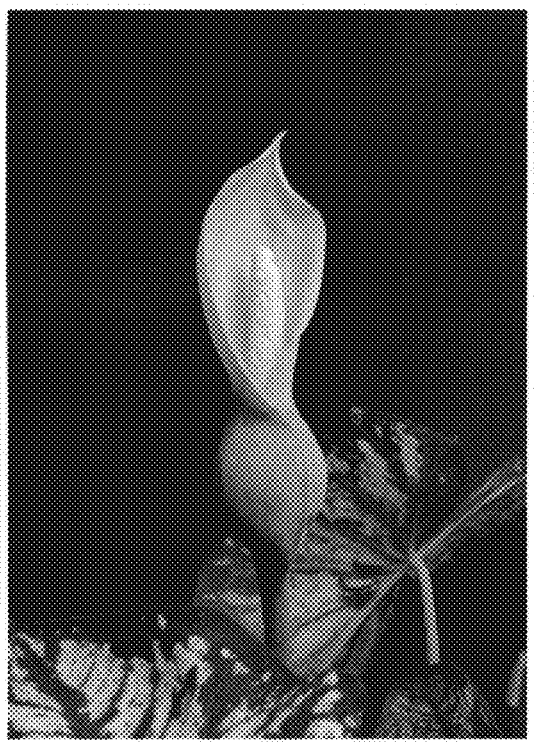

* * * * *